United States Patent [19]

Barcel et al.

[11] Patent Number: 5,014,720
[45] Date of Patent: May 14, 1991

[54] LEAD TO ELECTRODE JOINT ASSEMBLY AND METHOD OF MANUFACTURE THEREOF

[75] Inventors: James E. Barcel, Simi Valley, Calif.; Thomas M. Soukup, Lake Jackson, Tex.

[73] Assignee: Siemens-Pacesetter, Inc., Sylmar, Calif.

[21] Appl. No.: 461,703

[22] Filed: Jan. 8, 1990

[51] Int. Cl.⁵ .............................................. A61N 1/05
[52] U.S. Cl. ................................................. 128/786
[58] Field of Search ...................... 128/419 P, 784–786

[56] References Cited

U.S. PATENT DOCUMENTS 4,328,812 5/1982 Ufford et al. ........................ 128/786
4,667,686 5/1987 Peers-Trevarton ................. 128/785

Primary Examiner—William E. Kamm
Attorney, Agent, or Firm—Malcolm J. Romano

[57] ABSTRACT

A joint assembly which may be used for affixing a helically wound lead conductor coil to an electrode of a pacemaker. The electrode has a longitudinal bore and a coaxial counterbore. One end of the coil is fittingly attached to a reduced diameter end of a press tube. The outer diameter of the extreme outer surface of the coil on the press tube is slightly greater than the inner diameter of the counterbore in the electrode. The reduced diameter end of the press tube with the coil thereon is fittingly inserted into the counterbore. This results in a solid connection between the lead conductor coil and the electrode without causing any visible alteration of the outer surface of the electrode.

9 Claims, 2 Drawing Sheets

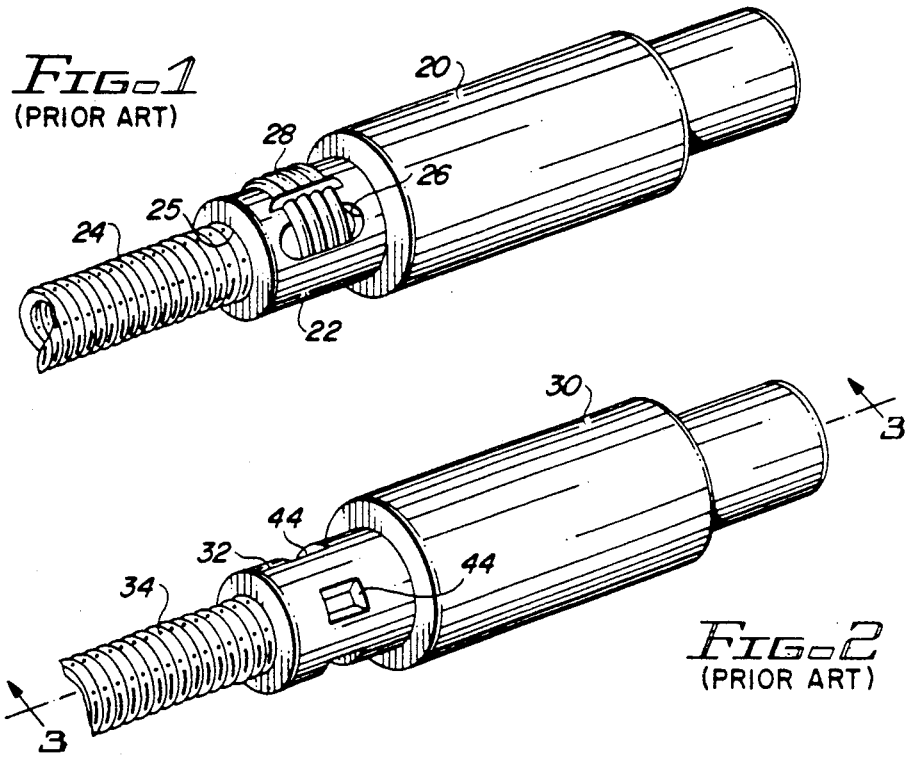
FIG-1 (PRIOR ART)
FIG-2 (PRIOR ART)
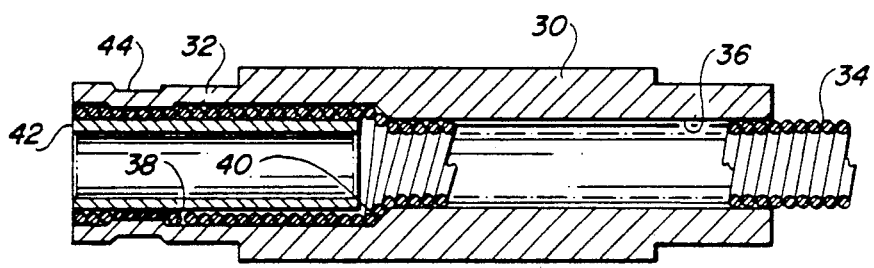
FIG-3 (PRIOR ART)
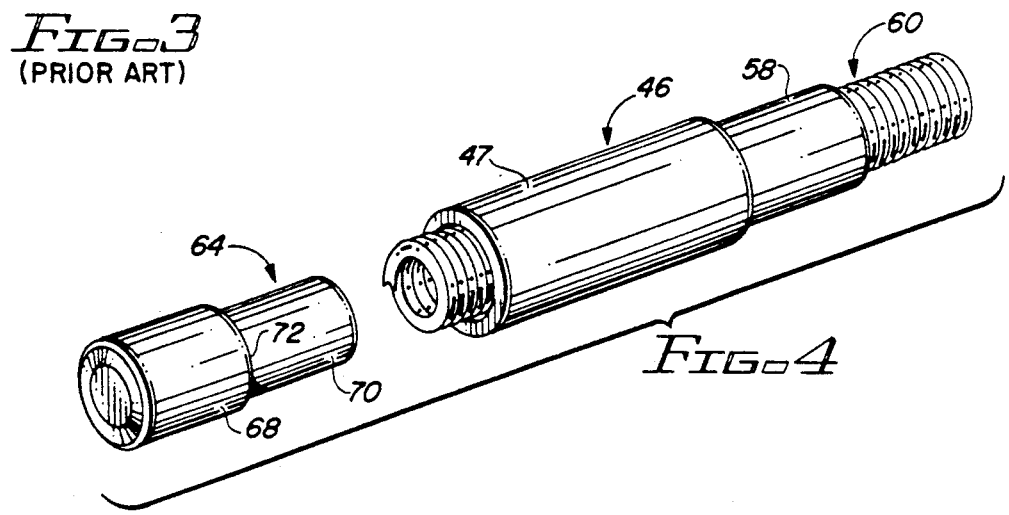
FIG-4

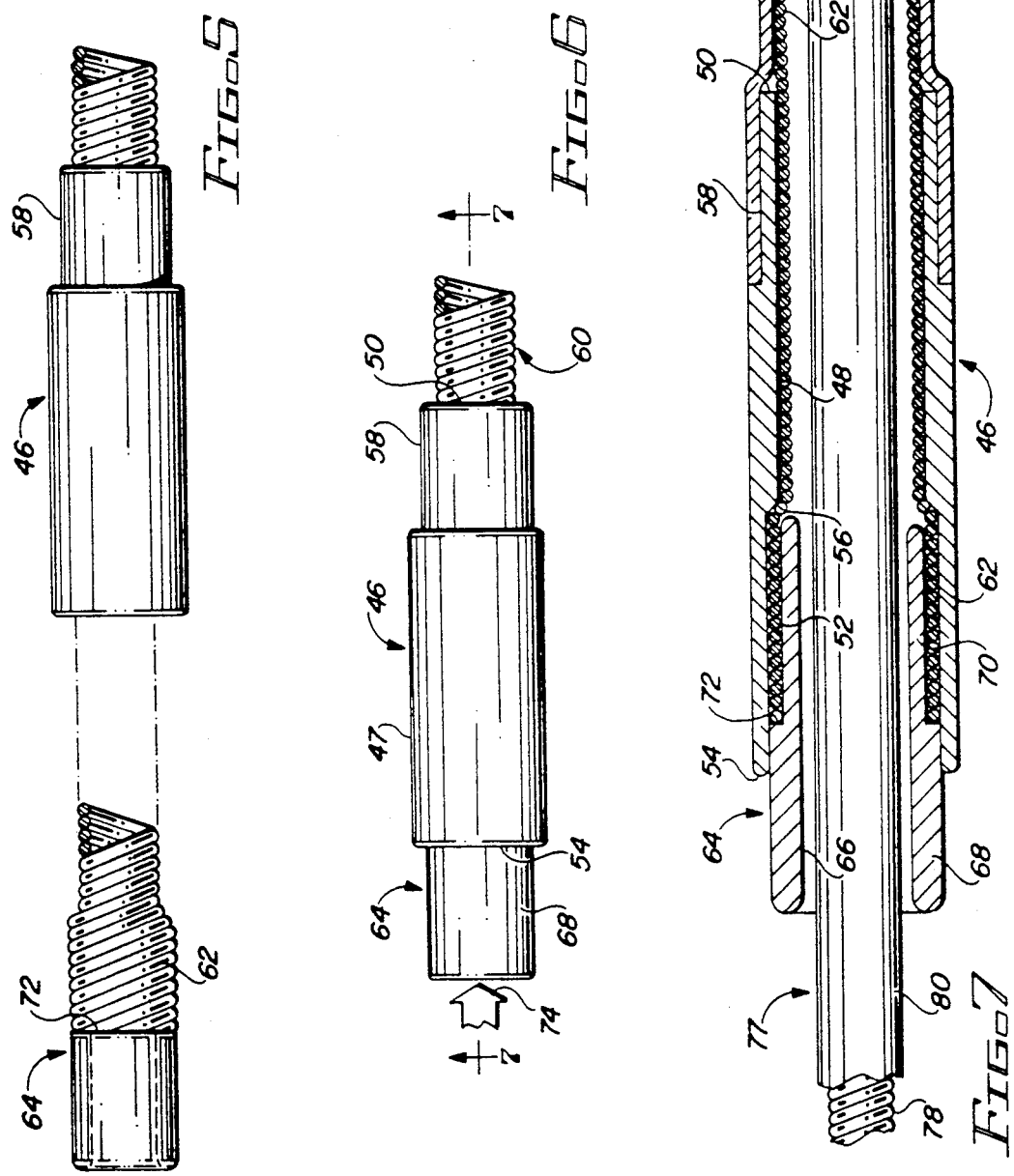

LEAD TO ELECTRODE JOINT ASSEMBLY AND METHOD OF MANUFACTURE THEREOF

BACKGROUND OF THE INVENTION

1. Field of the Invention

The present invention relates to a new and improved joint assembly and to a method of achieving the novel joint assembly. The joint assembly of the invention may have particular application to pacemakers, and more specifically, for connecting a helically wound lead conductor coil to an electrode.

2. State of the Prior Art

Electrical stimulation of body tissue and organs as a method of treating various pathological conditions is becoming quite commonplace. Such stimulation generally entails making some type of electrical contact with the body tissue or organ. In particular, with respect to the heart, electrical leads have been implanted by a thoracotomy in which an electrode formed on the end of the lead is physically implanted into the myocardial tissues.

Various electrode structures and various techniques for implanting those electrode structures into such body tissue as the heart, or myocardium, have been developed. Typically, electrodes attached to the heart are stimulated by a cardiac pacemaker which may be implanted within the patient's body.

Bipolar systems utilizing coaxial leads have come to be widely used. In coaxial leads, the two conductors are shaped into a small helix surrounded by a larger helix resulting in a much smaller pulse generator connector block. Nonetheless, there is continuing emphasis on developing leads and connectors of ever smaller sizes.

It is mandatory that the outer peripheral surface of the electrode remain unaffected following an operation of joining a lead to the electrode. For this reason, it has been customary to attach the lead, usually helically wound, to a reduced end portion of the electrode by spot or laser welding or, alternatively, by crimping. In either event, a minimum size limit has been effectively reached because of the nature of the design of those constructions.

Accordingly, efforts to achieve an acceptable connection with further miniaturization has required consideration of other concepts. It is in light of the current state of the art as just related that the present invention has been conceived and reduced to practice.

SUMMARY OF THE INVENTION

To this end, the present invention relates to a novel joint assembly which may be used for affixing a helically wound lead conductor coil to an electrode of a pacemaker. The electrode has a longitudinal bore and a coaxial counterbore. One end of the coil is fittingly attached to a reduced diameter end of a press tube. The outer diameter of the extreme outer surface of the coil on the press tube is slightly greater than the inner diameter of the counterbore in the electrode. The reduced diameter end of the press tube with the coil therein is fittingly inserted into the counterbore. This results in a solid connection between the lead conductor coil and the electrode without causing any visible alteration of the outer surface of the electrode.

The technique of the invention provides for maximum diametric reduction of the electrode, and therefore, maximum weight reduction. Both of these are important considerations when designing down-sized endocardial pacing leads. For example, the crimped electrode presently used has a diameter of approximately 0.094 inches. By contrast, the assembly of the invention could be as small as 0.75 inches in diameter while still employing the same components.

Furthermore, the invention simplifies known techniques and can result in a higher rate of manufacture and, therefore, productivity.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and, together with the description, serve to explain the principles of the invention in general terms. Like numerals refer to like parts throughout the disclosure.

BRIEF DESCRIPTION OF THE DRAWINGS

FIG. 1 is a perspective view depicting a prior art coil to electrode connection which has been accomplished by welding;

FIG. 2 is a perspective view of another prior art connection which has been accomplished by crimping;

FIG. 3 is a cross section view taken generally along line 3—3 in FIG. 2;

FIG. 4 is a perspective exploded view illustrating primary components of the invention;

FIG. 5 is a side elevation view illustrating one step of a method resulting in the connection of the invention;

FIG. 6 is a side elevation view of a completed connection of the invention; and

FIG. 7 is a cross section view taken generally along line 7—7 in FIG. 6.

DETAILED DESCRIPTION OF THE PREFERRED EMBODIMENT

Turn now to the drawings and, initially, to FIGS. 1–3 which depict known constructions. FIG. 1, for example, illustrates an electrode 20 with a reduced end 22 to which a multiple winding helical coil 24 is joined. The coil 24 extends into a longitudinal bore 25 formed in the electrode. The reduced end 22 of the electrode 20 is provided with an elongated aperture 26 through which a plurality of ends 28 from the coil 24 project. The ends 28 are then spot or laser welded to the outer surface of the reduced end 22.

Another type of known connection is illustrated in FIGS. 2 and 3. As in the instance of the electrode 20, an electrode 30 has a reduced end 32 to which a helical coil 34 is to be joined. Electrode 30 has a longitudinal bore 36 extending inwardly from one end and a counterbore 38 extending inwardly from an opposite end. The bore 36 and counterbore 38 meet at a modified shoulder 40 and the coil 34 is slidably received in the bore 36 and counterbore 38. A cylindrical crimp tube 42 is inserted into the counterbore 38 which enlarges the diameter of the coil 34 in the region of the counterbore 38. A suitable crimping tool is then employed to depress the reduced end 32 into firm engagement with the coil 34 at circumferentially spaced crimp regions 44 and the coil, in turn, into engagement with the crimp tube 42. For bipolar constructions, the inner diameter of the crimp tube 42 must be sufficiently large to slidably receive an inner coil and its insulation (not shown). The inner coil and insulation combination is also slidably receivable within the coil 3 both within the bore 36 and as the coil extends to a distant location. The counterbore 38 is provided to accommodate the addition of the crimp tube 42, but of necessity, causes a reduced thickness of material at the reduced end 32 of the electrode 30.

Thus, it will be appreciated that both the welded construction of FIG. and the crimped construction of FIGS. 2 and 3 have a number of drawbacks. In a first instance, it would be most difficult to reduce dimensions further without compromising the strength and integrity of the resulting electrode and its connection to the coil 34. Additionally, the connection is not a uniform one but is substantially limited to the weld regions and to the crimp regions 44.

Turn now to FIGS. 4–7 which illustrate a construction which avoids the drawbacks of the prior art as just described. For purposes of the invention, a tubular electrode 46 is provided which, in typical fashion, may be composed of a platinum iridium alloy. The electrode has a cylindrical outer surface 47 and is formed with a longitudinal bore 48 which extends inwardly from one end 50 and a counterbore 52 coaxial with the longitudinal bore 48 extending inwardly from an opposite end 54. The longitudinal bore 48 and counterbore 52 intersect at a modified shoulder 56. Additionally, the electrode is formed with a cylindrical undercut surface 58 adjacent the end 50 which is generally coaxial with the cylindrical outer surface 47.

A lead conductor 60 which may be formed as a multiple winding helical coil 62 is utilized by the invention and, in typical fashion, may be of MP 35N alloy manufactured by Latrobe Steel Company of Latrobe, Pa., or may be of other suitable metal. The coil 62 has a normal outer diameter slightly smaller than the inner diameter of the longitudinal bore 48 to enable slidable reception of the lead conductor 60 in the bore 48.

The invention also utilizes a cylindrical press tube 64 which has a longitudinal bore 66 which may have an inner diameter substantially equal to that of the coil 62. The press tube 64 may be composed of a platinum iridium alloy like the electrode 46 or of AISI Type 316L stainless steel, or of other suitable material. The press tube 64 is also characterized as having a major end 68 with a major outer peripheral surface having an outer diameter substantially equal to the inner diameter of the counterbore 52, a minor end 70 with a minor outer peripheral surface having an outer diameter greater than the inner diameter of the longitudinal bore 48, and an annular shoulder 72 at the interface between the major outer surface and the minor outer surface.

In accordance with the invention, as particularly well seen in FIG. 5, a proximal end of the coil 62 is threaded or otherwise forced onto the minor end 70 of the press tube 64 until it substantially engages the annular shoulder 72. This causes circumferential enlargement of the coil and the natural spring tension thereby created in the coil keeps it tightly affixed to the press tube. When the coil 62 is affixed to the press tube 64 in the manner illustrated in FIG. 5, it presents an outer surface having an extreme outer diameter slightly greater than the inner diameter of the counterbore 52.

A next step of the method of the invention is realized when the press tube 64 with coil 62 thereon is pressed in the direction of an arrow 74 such that the minor end 70 with coil 62 thereon is pressed into engagement with the counterbore 52. This step continues until a terminal surface of the minor end 70 is positioned proximate the shoulder 56. When this occurs, the minor end 70 is substantially coextensive with the counterbore 52. The interference fit which thereby results by reason of the engagement of the helical coil 62 with the counterbore 52 assures a strong and durable connection between the electrode and the lead connector 60. Additionally, the resultant connection presents no visible crimps or other assembly marks which would be detrimental to the operation of the electrode. Also a uniform firm mechanical and electrical connection is thereby achieved between the electrode 46 and the coil 62 across the entire region of the minor end 20, not merely at concentrated locations as in the prior art. Yet another benefit is the substantial reduction in diameter which is achieved by the connection of the invention as compared with the prior art.

Outer insulation tubing 76, which may be of polyurethane or other suitable insulating material, is fittingly applied to the surface 58 of the electrode 46 and generally overlies and insulates the coil 62 as it extends to a distant location.

As seen in FIG. 7, an inner lead conductor 77 may accompany the lead conductor 60. Its inner coil 78 and associated inner insulation 80 are slidably received within the bore 66 of the press tube 64 and within the interior of the coil 62.

Thus, the connection of the invention just described is strong and durable and of minimal diameter even as it provides for the inner lead conductor 77.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. A joint assembly comprising:
    a tubular electrode having a cylindrical outer surface, a first longitudinal bore therethrough, and a counterbore coaxial with said first longitudinal bore;
    a lead conductor formed as a helically would coil having a coil outer diameter and a coil inner diameter, said coil outer diameter being smaller than the inner diameter of said first longitudinal bore; and
    a cylindrical press tube having a second longitudinal bore with an inner diameter substantially equal to the coil inner diameter, a major end with a major outer peripheral surface having an outer diameter substantially equal to the inner diameter of said counterbore in said tubular electrode, a minor end with a minor outer peripheral surface having an outer diameter greater than the inner diameter of said first longitudinal bore, and an annular shoulder at the interface between said major outer surface and said minor outer surface;
    said coil being fittingly received on said minor outer peripheral surface of said press tube, said press tube with said coil thereon being joined with said electrode such that said coil is positioned between said counterbore of said electrode and said minor outer peripheral surface of said press tube;
    whereby said press tube with said coil thereon is fittingly joined with said electrode without disturbing said cylindrical outer surface of said electrode.

2. A joint assembly as set forth in claim 1, wherein said electrode has a cylindrical undercut surface coaxial with said cylindrical outer surface; and
including:
   a tubular insulative sheath fittingly received on said undercut surface and extending away therefrom and covering said coil.

3. A joint assembly as set forth in claim 1, wherein said electrode is composed of 90% platinum and iridium, said coil is composed of MP 35N alloy, and said press tube is composed of 316L stainless steel.

4. A joint assembly as set forth in claim 1, wherein said coil has a proximal end which is engaged with said annular shoulder on said press tube.

5. A joint assembly as set forth in claim 4, wherein said coil has a proximal end and a distal end and wherein said electrode has a first end, said counterbore being located adjacent said first end, and a second end spaced from said first end, said longitudinal bore being located adjacent said second end;
   said proximal end of said coil being spaced from said first end, said coil extending beyond said second end to the distal end thereof at a remote location.

6. A method of joining a helically wound wire coil to a tubular electrode comprising the steps of:
   (a) providing a helically wound coil having an inner and an outer diameter;
   (b) providing a tubular electrode with a first longitudinal bore therethrough and a counterbore coaxial with said first longitudinal bore;
   (c) providing a press tube having a second longitudinal bore having an inner diameter substantially equal to the inner diameter of said coil and a major end with a major outer peripheral surface having an outer diameter substantially equal to the inner diameter of said counterbore in said tubular electrode and a minor end with a minor outer peripheral surface having an outer diameter greater than the inner diameter of the first longitudinal bore;
   (d) fittingly mounting a free end of said coil onto the minor outer peripheral surface of the press tube such that a resulting outermost diameter of the wire coil positioned on the press tube is slightly greater than the inner diameter of the counter bore; and
   (e) pressing the press tube with the wire coil thereon into fitting engagement with said electrode until the minor end of the press tube is substantially coextensive with the counterbore, the wire coil being sandwiched between the counterbore of the electrode and the minor end of the press tube.

7. A method as set forth in claim 6, wherein the step of fittingly mounting a free end of said coil onto the minor outer peripheral surface of the press tube further comprises the step of overlying the wire coil substantially completely over the minor outer peripheral surface of the press tube.

8. A method as set forth in claim 6, wherein the electrode has a cylindrical outer surface and a cylindrical undercut surface coaxial with the outer surface; and
including the step of:
   (f) fittingly applying a tubular insulative sheath onto the undercut surface such that the sheath extends away from the electrode and covers the coil.

9. A method as set forth in claim 6, wherein the electrode has first and second spaced ends, the counterbore being located adjacent the first end and the longitudinal bore being located adjacent the second end; and
   wherein, after completion of step (e), one end of the coil is spaced from the first end and the coil extends beyond the second end; and
   wherein the electrode has a cylindrical outer surface and a cylindrical undercut surface coaxial with the outer surface; and
including the step of:
   (g) fittingly applying a tubular insulative sheath onto the undercut surface such that the sheath extends away from the electrode and covers the coil.

* * * * *